United States Patent
Ikoshi et al.

(10) Patent No.: US 8,497,235 B2
(45) Date of Patent: Jul. 30, 2013

(54) SOFTENER COMPOSITION COMPRISING ETHOXYLATED ESTERQUATS

(75) Inventors: Risa Ikoshi, Tokyo (JP); Takaya Sakai, Wakayama (JP); Makoto Kubo, Wakayama (JP)

(73) Assignee: Kao Corporation, Tokyo (JP)

( * ) Notice: Subject to any disclaimer, the term of this patent is extended or adjusted under 35 U.S.C. 154(b) by 198 days.

(21) Appl. No.: 13/133,979

(22) PCT Filed: Dec. 9, 2009

(86) PCT No.: PCT/JP2009/070929
§ 371 (c)(1),
(2), (4) Date: Jul. 15, 2011

(87) PCT Pub. No.: WO2010/067885
PCT Pub. Date: Jun. 17, 2010

(65) Prior Publication Data
US 2011/0263476 A1 Oct. 27, 2011

(30) Foreign Application Priority Data

Dec. 11, 2008 (JP) .................................. 2008-315423
Dec. 8, 2009 (JP) .................................. 2009-278170

(51) Int. Cl.
*C11D 1/62* (2006.01)

(52) U.S. Cl.
USPC ........... 510/515; 510/276; 510/287; 510/321; 510/329; 510/330; 510/504; 510/521

(58) Field of Classification Search
USPC ................. 510/276, 287, 321, 329, 330, 504, 510/515, 521
See application file for complete search history.

(56) References Cited

U.S. PATENT DOCUMENTS

| 6,780,833 B1 | 8/2004 | Hayashi et al. |
| 2003/0036499 A1 | 2/2003 | Ohtawa et al. |
| 2003/0060389 A1 | 3/2003 | Ushio et al. |
| 2003/0130162 A1 | 7/2003 | Llosas et al. |

FOREIGN PATENT DOCUMENTS

| CN | 1336973 A | 2/2002 |
| EP | 1354869 A1 | 10/2003 |
| JP | 5-98571 A | 4/1993 |
| JP | 5-148198 A | 6/1993 |
| JP | 7-18577 A | 1/1995 |
| JP | 2001-192966 A | 7/2001 |
| JP | 2002-284747 A | 10/2002 |
| JP | 2003-155668 A | 5/2003 |
| JP | 2003-519294 A | 6/2003 |
| JP | 2003-306474 A | 10/2003 |
| JP | 2008-162901 A | 7/2008 |

OTHER PUBLICATIONS

Computer-Generated Translation for JP-2008-162901-A, published Jul. 17, 2008.
Computer-Generated Translation for JP-5-98571-A, published Apr. 20, 1993.
Computer-Generated Translation for JP-7-18577-A, published Jan. 20, 1995.
Notification of First Office Action for corresponding Chinese Patent Application No. 200980149876.X, dated Sep. 5, 2012.
International Search Report dated Feb. 16, 2010 for PCT/JP2009/070929.

*Primary Examiner* — Charles Boyer
(74) *Attorney, Agent, or Firm* — Birch, Stewart, Kolasch & Birch, LLP

(57) ABSTRACT

The present invention provides a softener composition containing a specific bis(polyalkoxyalkanol) type quaternary ammonium salt represented by formula (I):

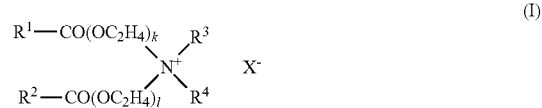

(I)

[wherein $R^1$ and $R^2$ may be the same as or different from each other and represent a hydrocarbon group having 11 to 23 carbon atoms, $R^3$ and $R^4$ may be the same as or different from each other and represent a hydrocarbon group having 1 to 4 carbon atoms which may have a hydroxyl group, k and l may be the same as or different from each other and represent an integer of 5 to 10 and $X^-$ represents an anion.]

5 Claims, No Drawings

SOFTENER COMPOSITION COMPRISING ETHOXYLATED ESTERQUATS

FIELD OF THE INVENTION

The present invention relates to a softener composition, more particularly to a liquid softener composition and a method for producing the same.

BACKGROUND OF THE INVENTION

Conventionally, a di-long chain alkyl ester or a di-short chain alkyl quaternary ammonium salt is used as a softener composition to soften fabrics. However, techniques of adding various additives and using a base to which an alkenyl group is introduced in order to yield the softness, water absorption and dispersibility of softeners have been known (for example, refer to JP-A 7-18575, JP-A 2001-192966, and JP-A2003-519294).

SUMMARY OF THE INVENTION

The present invention relates to a softener composition, containing a quaternary ammonium salt represented by formula (I):

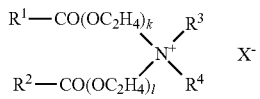

[wherein $R^1$ and $R^2$ may be the same as or different from each other and represent a hydrocarbon group having 11 to 23 carbon atoms, $R^3$ and $R^4$ may be the same as or different from each other and represent a hydrocarbon group having 1 to 4 carbon atoms which may have a hydroxyl group, k and l may be the same as or different from each other and represent an integer of 5 to 10 and $X^-$ represents an anion.]

Further, the present invention relates to a softener composition, containing a quaternary ammonium salt represented by the formula (I) [hereinafter referred to as quaternary ammonium salt (I)]:

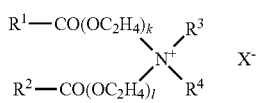

[wherein $R^1$ and $R^2$ may be the same as or different from each other and represent a hydrocarbon group having 11 to 23 carbon atoms, $R^3$ and $R^4$ may be the same as or different from each other and represent a hydrocarbon group having 1 to 4 carbon atoms which may have a hydroxyl group, k and l may be the same as or different from each other and represent an integer of 5 to 10 and $X^-$ represents an anion] and a quaternary ammonium salt represented by formula (II) [hereinafter referred to as quaternary ammonium salt (II)]:

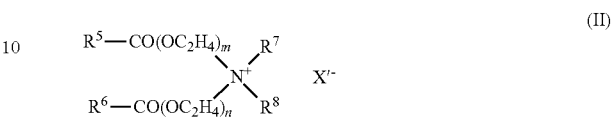

[wherein $R^5$ and $R^6$ may be the same as or different from each other and represent a hydrocarbon group having 11 to 23 carbon atoms, $R^7$ and $R^8$ may be the same as or different from each other and represent a hydrocarbon group having 1 to 4 carbon atoms which may have a hydroxyl group, m and n may be the same as or different from each other and represent an integer of 2 or 3 and $X'^-$ represents an anion.]

The present invention relates to a method for producing the softener composition of the above shown invention composition, including the following steps 1 and 2 as a step of producing the quaternary ammonium salt represented by the formula (I):

step 1: producing a bis(polyalkoxyalkanol)alkylamine or a bis(polyalkoxyalkanol)hydroxyalkylamine by a reaction of a halopoly alkoxy alkanol with an amine represented by the following formula (III):

$$R^3-NH_2 \quad (III)$$

[wherein $R^3$ represents a hydrocarbon group having 1 to 4 carbon atoms which may have a hydroxyl group.]; and step 2: esterifying the bis(polyalkoxyalkanol)alkylamine or the bis(polyalkoxyalkanol)hydroxyalkylamine produced in the step 1 with fatty acids or a derivative thereof and quaternizing the ester.

The present invention relates to use of the quaternary ammonium salt (I) for softener. The present invention relates to use of the composition containing the quaternary ammonium salt (I) and the quaternary ammonium salt (II) for softener.

DETAILED DESCRIPTION OF THE INVENTION

A process of specifying the number of EO addition moles and ensuring compatibility between softness and water absorption is not disclosed in JP-A 7-18575, JP-A 2001-192966, and JP-A 2003-519294.

The present invention provides a softener composition having excellent handling properties such that compatibility between a good softness and water absorption which is usually considered to be difficult is ensured, while exhibiting good softness, and good component dispersibility is exhibited without causing sequential thickening, more particularly a liquid softener composition.

According to the present invention, there is provided a softener composition having excellent handling properties such that compatibility between good softness and water absorption which is usually considered to be difficult is ensured, while exhibiting good softness, and good component dispersibility is exhibited without causing sequential thickening, more particularly a liquid softener composition.

<Quaternary Ammonium Salt (I)>

The quaternary ammonium salt (I) is a compound represented by the formula (I). From the viewpoint of softness, $R^1$ and $R^2$ in the formula (I) are a hydrocarbon group having 11 to 23 carbon atoms, preferably 15 to 21 carbon atoms, more preferably 15 to 17 carbon atoms, and are preferably an alkyl group or an alkenyl group. Specific examples thereof include various kinds of undecyl groups, various kinds of dodecyl groups, various kinds of tridecyl groups, various kinds of tetradecyl groups, various kinds of pentadecyl groups, various kinds of hexadecyl groups, various kinds of heptadecyl groups, various kinds of octadecyl groups, various kinds of nonadecyl groups, various kinds of eicosanyl groups, various kinds of heneicosanyl groups, various kinds of docosanyl groups, various kinds of tricosanyl groups, various kinds of undecenyl groups, various kinds of dodecenyl groups, various kinds of tridecenyl groups, various kinds of tetradecenyl groups, various kinds of pentadecenyl groups, various kinds of hexadecenyl groups, various kinds of heptadecenyl groups, various kinds of octadecenyl groups, various kinds of nonadecenyl groups, various kinds of icosenyl groups, various kinds of heneicosenyl groups, various kinds of docosenyl groups, and various kinds of tricosenyl groups. Preferable examples thereof include various kinds of pentadecyl groups, various kinds of heptadecyl groups, various kinds of nonadecyl groups, various kinds of heneicosanyl groups, various kinds of pentadecenyl groups, various kinds of heptadecenyl groups, various kinds of nonadecenyl groups, and various kinds of heneicosenyl groups. More preferable examples thereof include various kinds of pentadecyl groups, various kinds of heptadecyl groups, various kinds of pentadecenyl groups, and various kinds of heptadecenyl groups. Here, the term "various kinds" indicates to include the above shown straight chain or the above shown branched chain.

In the formula (I), $R^3$ and $R^4$ represent a hydrocarbon group having 1 to 4 carbon atoms which may have a hydroxyl group, preferably represent an alkyl group or a hydroxyalkyl group, particularly preferably represent a methyl group or a hydroxyethyl group. In the formula (I), k and l may be the same as or different from each other and respectively represent an integer of 5 to 10, preferably an integer of 5 to 8, more preferably an integer of 5 to 7, particularly preferably an integer of 5 or 6. $X^-$ represents an anion which is selected from the anions suitable for softeners. Examples of anions include halogen such as chlorine, bromine, and iodine; and ions such as methylsulfuric acid and ethyl sulfuric acid. Particularly, chloride ion and methylsulfuric acid ion are preferred.

<Quaternary Ammonium Salt (II)>

The softener composition of the present invention may contain the quaternary ammonium salt (II) represented by the formula (II) together with the quaternary ammonium salt (I). The content of both of the quaternary ammonium salt (I) and the quaternary ammonium salt (II) gives excellent softness on fibrous products, which is preferable. As for $R^5$ and $R^6$ in the formula (II), those exemplified by $R^1$ and $R^2$ in the formula (I) may be used and preferable examples thereof may be used. As for $R^7$ and $R^8$ in the formula (II), those exemplified by $R^3$ and $R^4$ in the formula (I) may be used and preferable examples thereof may be used. As for $X'^-$ in the formula (II), one exemplified by $X^-$ in the formula (I) may be used and preferable examples thereof may be used. m and n may be the same as or different from each other and respectively represent an integer of 2 or 3.

<Softener Composition>

The content of the quaternary ammonium salt (I) in the softener composition of the present invention is preferably from 1 to 40% by weight, preferably from 2 to 30% by weight, more preferably from 3 to 20% by weight, more preferably from 4 to 10% by weight, particularly preferably from 5 to 8% by weight. When the content of the quaternary ammonium salt (I) is 1% by weight or more, higher performance may be achieved. Meanwhile, the blending amount is 40% by weight or less, solution stability is more excellent, thereby making the production easy.

When the softener composition of the present invention contains the quaternary ammonium salt (I) and the quaternary ammonium salt (II), it may give higher softness as described above.

When the softener composition contains the quaternary ammonium salt (II), the total content of the quaternary ammonium salt (I) and the quaternary ammonium salt (II) in the softener composition is preferably larger than 1% by weight and 40% by weight or less, more preferably from 2 to 15% by weight. The weight ratio of the quaternary ammonium salt (I) and the quaternary ammonium salt (II) is preferably 99:1 to 50:50 (the quaternary ammonium salt (I): the quaternary ammonium salt (II)), more preferably 80:20 to 55:45, particularly preferably 70:30 to 55:45. As for the weight ratio, when the ratio of the quaternary ammonium salt (II) is 50 or less, the composition is excellent in water absorption and handling properties.

The softener composition of the present invention contains water. Usually, the balance of the composition is water. The pH of the softener composition of the present invention at 20° C. is preferably from 1.5 to 6. From the viewpoint of preservation and sterilizing properties, low pH is preferred. Too low a pH may cause decomposition of components which are usually blended in the composition. Therefore, the pH is more preferably from 1.5 to 5, further preferably from 2 to 4.5. In order to adjust the pH, any inorganic or organic acids and alkali may be used. Specific examples thereof include carboxylic acids such as hydrochloric acid, sulfuric acid, phosphoric acid, dialkyl sulfuric acid, alkyl sulfuric acid, dialkyl carbonic acid, para-toluenesulfonic acid, acetic acid, citric acid, malic acid, succinic acid, lactic acid, and glycolic acid; polymeric acrylic acid such as acrylic acid, hydroxy ethane diphosphonic acid, tripoliphosphoric acid, phytic acid; short-chain amine compounds such as ethylenediaminetetraacetic acid, triethanolamine, diethanolamine, dimethylamine, N-methylethanolamine, N-methyldiethanolamine, N-methyl-N-(2-hydroxyethyl)-N-(2-cyanoethyl)amine, N-methyl-N-(2-hydroxyethyl)propanediamine, 2,3-dihydroxy-N,N-dimethylpropylamine, N,N-di(2-hydroxyethyl) propanediamine; or alkylene oxide adducts thereof, long-chain amine compounds having 8 to 36 carbon atoms being bonded to nitrogen, or alkylene oxide adducts thereof. The above-described salts may also be used. Alkali metal hydroxide, alkali metal carbonate, alkali metal silicate or the like may be used. Among them, hydrochloric acid, methylsulfuric acid, sodium hydroxide, diethanolamine, and triethanolamine are preferred. The present invention further contains at least one selected from components (c-1) and (c-2) as component (c) so that the preserving and sterilizing property of the composition may be improved.

The component (c-1) is an alcohol having 1 to 8 carbon atoms. Specific examples thereof include ethanol, isopropanol, propylene glycol, diethylene glycol, dipropylene glycol, 1,2-pentanediol, hexylene glycol, trimethylpentanediol, benzyl alcohol, diethylene glycol monobutyl ether, 2-phenoxyethanol, and 2-phenylethanol. Among them, compounds not containing a nitrogen atom, such as ethanol, isopropanol, propylene glycol, 1,2-pentanediol, hexylene glycol, benzyl alcohol, diethylene glycol monobutyl ether, and 2-phenoxyethanol are preferred. Two or more of these may be combined for use. The blending amount of the component (c-1) in the composition is preferably from 0.1 to 60% by weight, more preferably from 1 to 40% by weight, particularly preferably from 1 to 25% by weight. As for a lower alcohol, alcohols modified by modifying agents such as denatonium benzoate, 8-acetylated sucrose, brucine, orange, and citrus may be used.

The component (c-2) is a compound selected from benzoic acids and phenol compounds. Examples thereof include benzoic acid or a salt thereof, salicylic acid or a salt thereof, para-hydroxybenzoic acid or a salt thereof, methyl parahydroxybenzoate, ethyl para-hydroxybenzoate, propyl parahydroxybenzoate, butyl parahydroxybenzoate, benzyl parahydroxybenzoate, 3-methyl-3-isopropylphenol, o-phenylphenol, 2-isopropyl-5-methylphenol, resorcin, cresol, and 2,6-di-tert-butyl-p-cresol. Among them, benzoic acid and 2,6-di-tert-butyl-p-cresol are preferred. One or two or more of these may be combined for use. The blending amount of the component (c-2) in the composition is preferably from 0.0001 to 5% by weight, more preferably from 0.0003 to 3% by weight, particularly preferably from 0.0005 to 1% by weight.

The softener composition of the present invention has excellent handling properties. In order to further improve dispersibility, alkylene oxide adducts of alcohol, amine or fatty acid may be used. However, it is possible to decrease the added amount more greatly than a usual amount. The carbon chain of the alkylene oxide adducts of alcohol, amine or fatty acid may be branched or straight, and may be unsaturated. Further, the carbon chain may have distribution. The carbon chain has preferably 6 to 20 carbon atoms, more preferably 8 to 18 carbon atoms. When the carbon chain is straight, the carbon chain has preferably 6 to 14 carbon atoms, more preferably 8 to 12 carbon atoms, even more preferably 8 to 10 carbon atoms. When the carbon chain is branched, the carbon chain has preferably 6 to 17 carbon atoms, more preferably 9 to 17 carbon atoms, and even more preferably 13 carbon atoms. As a raw material, Exxal (manufactured by Exon Chemicals), Lutensol TO (manufactured by BASF), Oxocol C13 (manufactured by Kyowa Hakko Kirin Co., Ltd.) or the like may be used. Particularly, in the case of the alkylene oxide adduct of an alcohol, a primary or secondary alcohol may also be used. The primary alcohol provides a resulting composition with a good dispersibility of the blended components. Alcohol having 13 carbon atoms is produced from a raw material of dodecen. The starting material thereof may be butylene or propylene. When the carbon chain contains an unsaturated group, the carbon chain having 18 carbon atoms is preferred. The stereoisomer structure of the unsaturated group may be a cis- or trans-isomer or a mixture thereof. Particularly, the ratio of the cis- or trans-isomer is preferably 25/75 to 100/0 (weight ratio). Alkylene oxide is preferably ethyleneoxide (EO), and propylene oxide (PO) or butylene oxide (BO) may be added together with ethyleneoxide. The average addition mole number of EO is from 10 to 100 mol, preferably from 20 to 80 mol, particularly preferably from 30 to 60 mol. The average addition mole number of PO or BO to be added together with EO is from 1 to 5, preferably from 1 to 3. In this case, PO or BO may be added after addition of EO or EO may be added after addition of PO or BO. Examples thereof include an adduct having 9 moles on the average of EO and 1 mole on the average of PO, added to nonyl alcohol, an adduct having 40 moles on the average of EO, added to primary isononyl alcohol, an adduct having 20 moles on the average of EO, added to primary isodecyl alcohol, an adduct having 20 moles on the average of EO, added to lauryl alcohol, an adduct having 60 moles on the average of EO, added to primary isohexadecyl alcohol, an adduct having 40 moles on the average of EO, added to primary isotridecyl alcohol, an adduct having 60 moles on the average of EO, added to beef tallow alkylamine, an adduct having 60 moles on the average of EO, added to beef tallow alkylamine, an adduct having 50 moles on the average of EO, added to oleylamine, and an adduct having 20 moles on the average of EO, added to lauric acid. Usable examples thereof include Emalex series (manufactured by NIHON EMULSION Co., Ltd.), Emulmin series (manufactured by Sanyo Chemical Industries, Ltd.), TDA series and Esomin series (manufactured by Lion Corporation.), Softanol series such as Softanol 300 (manufactured by NIPPON SHOKUBAI CO., LTD.), and Lutensol series (manufactured by BASF). The blending amount of the alkylene oxide adducts of alcohol, amine or fatty acid is preferably from 0 to 5% by weight, more preferably from 0 to 2% by weight, particularly preferably from 0 to 1% by weight based on the whole composition.

The softener composition of the present invention has low viscosity and excellent handling properties. In order to further decrease the viscosity of the composition, inorganic or organic salts [excluding the quaternary ammonium salts (I) and (II)] may be used in a small amount. Among these inorganic or organic salts, an alkali metal salt or an alkaline earth metal salt is preferred. Specific examples thereof include sodium chloride, potassium chloride, calcium chloride, magnesium chloride, aluminium chloride, sodium sulfate, magnesium sulfate, potassium sulfate, sodium nitrate, magnesium nitrate, sodium p-toluenesulfonate, sodium glycolate, sodium acetate, potassium acetate, potassium glycolate and sodium lactate. Calcium chloride and magnesium chloride are preferred. These blending amounts allow the usual amount to be reduced greatly and they are set to preferably 0 to 2% by weight, more preferably 0.001 to 1% by weight, further preferably 0.01 to 0.5% by weight. The ratio of these inorganic or organic salts is preferably from 0.001 to 10% by weight, more preferably from 0.005 to 5% by weight, particularly preferably from 0.05 to 1% by weight based on the content of the quaternary ammonium salt (I) in the softener composition or the total content of the quaternary ammonium salt (I) and the quaternary ammonium salt (II).

When the softener composition of the present invention is used for fibrous products such as clothes, silicone selected from dimethylpolysiloxane and modified-dimethylpolysiloxane having various kinds of organic functional groups may be used alone or as a mixture of two or more kinds thereof at an arbitrary ratio in order to give tightness and improve ironing smoothness. When silicone is dimethylpolysiloxane, the degree of polymerization of silicone is preferably in the range of 10 to 1,000,000 mPa·s, more preferably in the range of 10 to 100,000 mPa·s, even more preferably in the range of 10,000 to 100,000 mPa·s. When silicone is a modified dimethylpolysiloxane, examples thereof include silicones produced by modifying two or more of organic functional groups such as amino, amide, alkyl, aralkyl, carboxyl, fluoroalkyl, higher alcohol ester, polyether, epoxy, carbinol, mercapto, phenol, methacrylic, aminopolyether, amidopolyether, and alkyl alcohol. One or two or more thereof are selected. The bonding position of the organic functional group to the main chain of dimethylpolysiloxane may be the side chain or the end. When the organic functional group is bonded to the end, it may be bonded to either one end or both ends. The weight ratio of the organic functional group to dimethylpolysiloxane may be optional and is not particularly limited. As the modified-dimethylpolysiloxane, dimethylpolysiloxane hydride, which is a precursor for introducing an organic functional group, or hydroxylated dimethylpolysiloxane may be independently used. Alternatively, they may be mixed with a modified-dimethylpolysiloxane having an organic functional group.

Preferable examples of silicones include dimethyl silicone, polyoxyethylene-modified-silicone, silicone containing a hydrogen group or a hydroxyl group, and the emulsified products thereof. The blending ratio of these silicone compounds in the composition may be preferably from 0.1 to 20% by weight, more preferably from 0.3 to 10% by weight.

In order to improve preservation and sterilizing properties, at least one of the following compounds may be used preferably in an amount of 0 to 0.5% by weight, more preferably 0 to 0.1% by weight based on the amount of the composition: sodium pyrithione, 1,3-bis(hydroxymethyl)-5,5-dimethyl-2,4-imidazolidinedione, dimethylol dimethylhydantoin, DMDM hydantoin (manufactured by Lonza or Glydant Plus); N-[1,3-bis(hydroxymethyl)-2,5-dioxo-4-imidazolidinyl]-N,N'-bis(hydroxymethyl)urea (generally marketed under the name of diazolidinyl urea); N,N'-methylene-bis{N'-[1-(hydroxymethyl)-2,5-dioxo-4-imidazolidinyl]urea}; imidazolidinedione compounds generally known as imidazolidinyl urea; polymethoxide bicyclic oxazolidine compounds; low-molecular-weight aldehydes such as formaldehyde and glutaraldehyde; polyaminopropylbiguanide known as polyhexamethylene biguanide having formula: $HCl.NH_2-(CH_2)_3-[-(CH_2)_3-NH-C(=NH)-NH-C(=NH.HCl)-NH-(CH_2)_3-]_x-(CH_2)_3-NH-C(=NH)-NH.CN$; 1,1'-hexamethylene-bis(5-(p-chlorophenyl)biguanide generally known as chlorhexidine; acetic acid, digluconic acid, digluconate (i.e., salt) and diacetates thereof, commercially available products such as Proxel IB, manufactured by Avecia Ltd.; 1-(3-chloroallyl)-3,5,7-triaza-1-azoniaadamantane chloride, for example, marketed under the trade name of Dowicil200 from Dow Chemical; dehydroacetic acid, 4,4'-diamidino-α,ω-diphenoxypropane diisethionate generally known as propamidine isethionate; 4,4'-diamidino-α,ω-diphenoxyhexane diisethionate generally known as hexamidine isethionate; imidazole- or thiazole-based antibacterial agents such as 12-(4'-thiazolyl)-benzimidazole, 2-(4-thiocyanomethylthio)benzothiazole, and methyl-2-benzimidazole carbamide; 1,1,1-trichloro-2-methylpropan-2-ol, chlorobutanol generally known as chlorobutanol, 4,4'-(trimethylenedioxy)-bis-(3-bromobenzamidine) diisethionate, or dibromopropamidine; 3,4,4'-trichlorocarbanilide or N-(4-chlorophenyl)-N'-(3,4-dichlorophenyl)urea which is known as trichlocarban; 2,4,4'-trichloro-2'-hydroxydiphenylether (generally known as triclosan); and the like.

In order to make a user know use of a product, perfumes may be used. One or two or more of the following components may be mixed for use: hydrocarbons generally used for softener compositions, such as aliphatic hydrocarbon, terpene hydrocarbon, and aromatic hydrocarbon; alcohols such as aliphatic alcohol, terpene alcohol, and aromatic alcohol; ethers such as aliphatic ether and aromatic ether; oxides such as aliphatic oxide and oxides of terpenes; aldehydes such as aliphatic aldehyde, terpene-based aldehyde, hydrogenated aromatic aldehyde, and thioaldehyde, aromatic aldehyde; ketones such as aliphatic ketone, terpene ketone, hydrogenated aromatic ketone, aliphatic cyclic ketone, non-benzene-based aromatic ketone, and aromatic ketone; acids such as acetals, ketals, phenols, ether phenols, fatty acid, terpene-based carboxylic acid, hydrogenated aromatic carboxylic acid, and aromatic carboxylic acid; lactones such as acid amides, aliphatic lactone, macrocycliclactone, terpene-basedlactone, hydrogenated aromatic lactone, and aromatic lactone; esters such as aliphatic ester, furan-based carboxylic acid ester, aliphatic cyclic carboxylic acid ester, cyclohexyl carboxylic acid ester, terpene-based carboxylic acid ester, and aromatic carboxylic acid ester; synthetic perfumes such as nitrogen-containing compounds, for example, nitro musks, nitrile, amine, pyridines, quinolines, pyrrole, and indole; natural perfumes from animals and plants; and prepared perfumes containing the natural perfumes and/or synthetic perfumes. Usable examples thereof include perfumes described in "Synthetic Perfume, Chemistry and Knowledge on products", Motoichi Indo, The Chemical Daily Co., Ltd., 1996 and "Perfume and Flavor Chemicals", STEFFEN ARCTANDER, MONTCLAIR, N.J. 1969.

In order to improve the appearance of the composition, at least one water-soluble dye selected from an acid dye, a direct dye, a basic dye, a reactive dye, a mordant dye, and an acid mordant dye may be added. Specific examples of the dye to be added are described in Dye handbook manual (edited by Society of Synthetic Organic Chemistry, Japan, Maruzen, issued on Jul. 20, 1970).

In addition to the above-described components, known components which are blended with usual softener compositions may be added to the softener composition of the present invention as other optional components in a range not impairing the effect of the invention. Examples of optional components include di-long-chain alkyldimethyl quaternary ammonium salt, mono-long-chain alkyltrimethyl quaternary ammonium salt; higher fatty acids such as stearic acid, oleic acid, and palmitic acid; fatty acid methyl esters such as stearic acid methyl ester, oleic acid methyl ester, palmitic acid methyl ester which are esters of the lower alcohols thereof preferably in an amount of 0 to 2% by weight; nonionic surfactants such as fatty acid glycerol ester which is ester of stearic acid, glycerin or pentaerythritol preferably in an amount of 0 to 1.0% by weight; higher alcohols such as stearyl alcohol, palmityl alcohol, oleyl alcohol, and primary or secondary isotridecyl alcohol preferably in an amount of 0 to 3.0% by weight; low-temperature stabilizers such as ethylene glycol and glycerin preferably in an amount of 0 to 10% by weight; hydroxy ethane diphosphonic acid (Feliox CY-115, manufactured by Lion Corporation); ethylenediaminetetraphosphonic acid (Dequest2041, manufactured by Monsanto); phosphonic-type chelating agents such as D-2000, 2010, 2066; chelating agents such as ethylenediaminetetraacetic acid, nitrilotriacetic acid, citric acid, protocatechuic acid, tripoliphosphoric acid, ethylenediamine disuccinic acid, methylglycinediacetic acid, iminodisuccinic acid, hydroxyiminodisuccinic acid, aspartic acid, polyglyoxylic acid, polyaspartic acid, polyacrylic acid, copolymer of acrylic acid and maleic acid (the molecular weight of polymer is arbitrary) and salts thereof such as sodium preferably in an amount of 0 to 5.0%; antioxidants preferably in an amount of 0 to 0.1% by weight; hydrocarbons which are liquid at ordinary temperature, such as liquid paraffin preferably in an amount of 0.01 to 2.0% by weight; ureas, pigments, cellulose derivatives, ultraviolet absorbers, and fluorescent brighteners.

The usable concentration of the composition of the present invention varies depending on the application and the form to be used. When the composition of the present invention is used for fibrous products such as clothes, the composition is preferably diluted so that the concentration of the composition of the present invention to rinsing water is from 0.001 to 3% by weight, preferably from 0.01 to 1% by weight.

<Method for Producing Softener Composition>

The softener composition of the present invention may be produced by the method for producing a softener composition including the steps 1 and 2:

step 1: producing bis(polyalkoxyalkanol)alkylamine or bis(polyalkoxyalkanol)hydroxyalkylamine by a reaction of halopoly alkoxy alkanol with amine represented by the following formula (III):

$$R^3-NH_2 \qquad (III)$$

[wherein $R^3$ represents a hydrocarbon group having 1 to 4 carbon atoms which may have a hydroxyl group.]; and
step 2: esterifying bis(polyalkoxyalkanol)alkylamine or bis(polyalkoxyalkanol)hydroxyalkylamine produced in the step 1 with fatty acids or the derivatives thereof and quaternizing the ester.

This method allows for an efficient production of a quaternary ammonium salt having an oxyethylene chain without the EO distribution which is the quaternary ammonium salt (I).

In the step 1, bis(polyalkoxyalkanol)alkylamine or bis(polyalkoxy alkanol)hydroxyalkylamine is produced by a reaction of halopoly alkoxy alkanol with amine represented by the formula (III).

As halopoly alkoxy alkanol to be used in the step 1, halopoly alkoxy alkanol represented by the following formula (IV) is listed.

$$Y(CH_2CH_2O)_iH \qquad (IV)$$

[wherein Y represents a halogen atom and i represents an integer of 5 to 10.]

Specific examples of the compound represented by formula (IV) include polyoxyethylene [in the formula (IV), i represents 4.], 2-chloroethanol, polyoxyethylene [in the formula (IV), i represents 5.], and 2-chloroethanol.

In the step 1, 0.3 to 2 equivalents, preferably 0.4 to 1.8 equivalents of halopoly alkoxy alkanol (i.e., halopoly alkoxy alkanol/amine) is used based on the amine represented by the formula (III). In the step 1, water and an alcohol such as ethanol may be used as a reaction solvent. The reaction temperature in the step 1 is from 70 to 110° C., preferably from 80 to 100° C. The reaction time is preferably from 1 to 5 hours.

In the step 1, bis(polyalkoxyalkanol)alkylamine or bis(polyalkoxyalkanol)hydroxyalkylamine is obtained at a high yield by using the two-stage reaction below.

The first stage: Amine represented by the formula (III) is reacted with 0.3 to 0.6 equivalent of halopoly alkoxy alkanol (preferably, at 90 to 110° C., for 1 to 5 hours), followed by neutralization and removal of salt.

The second stage: Thereafter, 0.5 to 0.9 equivalent of halopoly alkoxy alkanol to mono-(polyalkoxyalkanol) is further added to the obtained mixture of di-(polyalkoxyalkanol) and mono-(polyalkoxyalkanol), which is reacted in water or an alcohol at 70 to 90° C. for 1 to 3 hours, followed by distillation.

The quaternary ammonium salt (II) may be produced in the same manner as the quaternary ammonium salt (I) by performing the step 3 of producing bis(polyalkoxyalkanol)alkylamine or bis(polyalkoxyalkanol)hydroxy alkylamine by a reaction of halopoly alkoxy alkanol, preferably halopoly alkoxy alkanol represented by the following formula (V), with amine represented by the formula (III) and the step 4 of esterifying bis(polyalkoxyalkanol)alkylamine or bis(polyalkoxyalkanol)hydroxyalkylamine which are produced by the step 3 with fatty acid or a derivative thereof and quaternizing the ester. Therefore, as for the softener composition containing the quaternary ammonium salt (II), the above-described steps may be used as steps 3 and 4 for producing the quaternary ammonium salt (II), in addition to the steps 1 and 2.

$$Y'(CH_2CH_2O)_jH \qquad (V)$$

[wherein Y' represents a halogen atom and j represents an integer of 2 or 3.]

Specific examples of the compound represented by formula (V) include 2-(2-chloroethoxy)ethanol, polyoxyethylene [in the formula (V), j is 2], and 2-chloroethanol.

Excessive amounts of halopoly alkoxy alkanol and unreacted amine may be removed by purifying them by distillation or the like.

In the step 2 or 4, bis(polyalkoxyalkanol)alkylamine or bis(polyalkoxyalkanol)hydroxyalkylamine (hereinafter referred to as intermediate amine) obtained in the step 1 or 3 is esterified with fatty acid or the derivatives thereof and then quaternized with alkyl halide.

In the esterification, higher fatty acid having 12 to 24 carbon atoms, preferably 16 to 22 carbon atoms, more preferably 16 to 18 carbon atoms or the derivatives thereof are used. Specific examples thereof include fatty acids obtained by purification, hydrogenation or partial hydrogenation of higher fatty acids such as myristic acid, palmitic acid, palmitoleic acid, stearic acid, oleic acid, linoleic acid, linolenic acid; and natural oils and fats such as beef tallow, lard, palm oil, and soybean oil. The derivatives of fatty acids are alkyl ester of the fatty acid, acid chloride, and acid anhydride.

In either the step 2 and the step 4, as for esterification conditions, the molar ratio of intermediate amine to fatty acid or the derivatives thereof is preferably 1:2 to 1:2.2 (intermediate amine:fatty acid or the derivatives thereof). In the esterification reaction, neither a solvent nor a catalyst is usually used. The temperature of the esterification reaction is preferably from 160 to 220° C. The progress and termination of esterification reaction may be confirmed by reduction of the hydroxyl value of amines or reduction of the acid number of fatty acids.

The obtained ester is quaternized after the esterification. When quaternizing, a usual method for reacting quaternizing agents such as alkyl halide (methyl chloride etc.) and alkylsulfuric acid may be used. In this regard, a quaternizing agent having a hydrocarbon group having 1 to 4 carbon atoms which may have a hydroxyl group is used.

A mixture containing the quaternary ammonium salt (I) is produced in the steps 1 and 2, while a mixture containing the quaternary ammonium salt (II) is produced in the steps 3 and 4. These mixtures may be suitably purified by a usual method such as crystallization. The softener composition of the present invention may be produced by using the quaternary ammonium salt (I) obtained in such a manner and the quaternary ammonium salt (II) of the softener composition of the present invention as a blending component.

EXAMPLES

The present invention will be described with reference to the following examples. The examples will not limit the present invention, just exemplifying the invention.

Preparation Example 1

34 g of 41% monomethylamine solution, 62 g of 2-(2-(2-(2-(2-chloro)ethoxy)ethoxy)ethoxy)ethoxyethanol [in the formula (IV), i is a compound having an integer of 6], and 80 g of water were introduced into a pressure-proof reaction vessel and were reacted at 110° C. for 4 hours, a sodium hydroxide solution (equivalent to a chloromer content) was added thereto, and the produced hydrochloric acid was neutralized. The reaction mixture was transferred to another reaction vessel and 27 g of chloromer-2-(2-(2-(2-(2-chloro)ethoxy)ethoxy)ethoxy)ethoxyethanol [in the formula (IV), i is a compound having an integer of 6] was added thereto and was reacted at 80° C. for 1 hour. Thereafter, a sodium hydroxide solution in an amount equivalent to chloromer-2-(2-(2-(2-(2-chloro)ethoxy)ethoxy)ethoxy)ethoxy)ethoxyethanol, which had been added, was added dropwise over 30 minutes. After aging for 30 minutes, the removal of solvent and salt was performed. Then, dimer-(bis(2-(2-(2-(2-(2-ethoxy)ethoxy)ethoxy)ethoxy)ethoxyethanol)methylamine) was isolated by distillation. The product was confirmed by NMR. Then, 37 g of the obtained dimer was reacted with 59 g of methyl stearate at 155° C. and 20 Torr (2.7 kPa) for 24 hours. After the completion of the reaction, an excessive amount of methyl stearate was removed by topping and a diesterified product of bis(2-(2-(2-(2-(2-ethoxy)ethoxy)ethoxy)ethoxyethanol)methylamine was obtained. Subsequently, 51 g of the diesterified product thus obtained was dissolved in 84 g of isopropyl alcohol and was charged into a pressure-proof vessel. Then, 13 g of methyl chloride was added thereto and the mixture was reacted at 88° C. for 5.5 hours to quaternize it. The reaction mixture was crystallized in cold acetone and dried to obtain the quaternary ammonium salt represented by the formula (I). The products was identified with NMR and analysis of oils and fats. The structure of the quaternary ammonium salt is shown in Table 1.

Preparation Example 2

A quaternary ammonium salt of Preparation example 2 was synthesized in the same manner as Preparation example 1 except that methyldiethanolamine was used in place of bis(2-(2-(2-(2-(2-ethoxy)ethoxy)ethoxy)ethoxy)ethoxyethanol)methylamine. The structure of the quaternary ammonium salt is shown in Table 1.

Preparation Example 3

Cation of Preparation example 3 was synthesized in the same manner as Preparation example 1 except that 2-(2-chloroethoxy)ethanol [in the formula (V), j is a compound having an integer of 2] was used in place of 2-(2-(2-(2-(2-chloro) ethoxy)ethoxy)ethoxy)ethoxy)ethoxyethanol. The structure of the quaternary ammonium salt is shown in Table 1.

Preparation Example 4

Cation of Preparation example 4 was synthesized in the same manner as Preparation example 1 except that 2-(2-(2-chloro)ethoxy)ethoxy)ethanol [in the formula (V), j is a compound having an integer of 3] was used in place of 2-(2-(2-(2-(2-chloro) ethoxy)ethoxy)ethoxy)ethoxy)ethoxyethanol. The structure of the quaternary ammonium salt is shown in Table 1.

Preparation Example 5

34 g of 41% monomethylamine solution, 53 g of 2-(2-(2-(2-(2-chloro) ethoxy)ethoxy)ethoxy)ethoxyethanol [in the formula (IV), i is a compound having an integer of 5], and 80 g of water were introduced into the pressure-proof reaction vessel and were reacted at 110° C. for 4 hours, a sodium hydroxide solution (equivalent to a chloromer content) was added thereto, and the produced hydrochloric acid was neutralized. The reaction mixture was transferred to another reaction vessel and 23 g of chloromer-2-(2-(2-(2-(2-chloro) ethoxy)ethoxy)ethoxy)ethoxyethanol [in the formula (IV), i is a compound having an integer of 5] was added thereto and the mixture was reacted at 80° C. for 1 hour. Thereafter, a sodium hydroxide solution in an amount equivalent to chloromer-2-(2-(2-(2-(2-chloro) ethoxy)ethoxy)ethoxy)ethoxy-ethanol, which had been added, was added dropwise over 30 minutes. After aging for 30 minutes, the removal of solvent and salt was performed, and then dimer-(bis(2-(2-(2-(2-ethoxy)ethoxy)ethoxy)ethoxyethanol)methylamine) was isolated by distillation. The product was confirmed by NMR. Then, 40 g of the obtained dimer was reacted with 75 g of methyl stearate at 155° C. and 20 Torr (2.7 kPa) for 24 hours. After the completion of the reaction, an excessive amount of methyl stearate was removed by topping and a diesterified product of bis(2-(2-(2-(2-ethoxy)ethoxy)ethoxy)ethoxyethanol)methylamine was obtained. Subsequently, 60 g of the diesterified product thus obtained was dissolved in 84 g of isopropyl alcohol and was charged into a pressure-proof vessel. Then, 10 g of methyl chloride was added thereto and the mixture was reacted at 88° C. for 5.5 hours to quaternize it. The reaction mixture was crystallized in cold acetone and dried to obtain the quaternary ammonium salt represented by the formula (I). The identification of the products was performed by NMR and analysis of oils and fats. The structure of the quaternary ammonium salt is shown in Table 1.

Example 1

The quaternary ammonium salt and calcium chloride obtained in Preparation example 1, having a composition of Table 1, were dispersed in ion exchange water to produce a liquid softener composition.

Example 2

The quaternary ammonium salt obtained in Preparation example 1 and the quaternary ammonium salt and calcium chloride obtained in Preparation example 3, having a composition of Table 1, were dispersed in ion exchange water to produce a liquid softener composition.

Example 3

The quaternary ammonium salt and calcium chloride obtained in Preparation example 5, having a composition of Table 1, were dispersed in ion exchange water to produce a liquid softener composition.

Comparative Examples 1 to 3

Liquid softener compositions were produced in the same manner as Example 1 except that the quaternary ammonium salts obtained in Preparation examples 2 to 4 were used.
(Evaluation)
(1) Dispersibility and Handling Properties
Dispersibility was evaluated based on easiness of preparation of dispersion liquid and the thickened condition after the preparation was observed. A composition which was not thickened even in a cooled state after the preparation was judged as being excellent in handling properties.
(2) Softness and Water Absorption
Commercially available cotton towels (T. W220, white, manufactured by Takei Towel Co., Ltd.) were washed repeatedly 5 times using a commercially available detergent (trademark: Attack, manufactured by Kao Corporation) to remove the starch of the clothes. The towels were stirred in tap water at 20° C. for 5 minutes using 0.1% by weight of the liquid softener with the composition of Table 1 (by weight to a towel) so as to have a bath ratio of 30 L/kg (by weight of a towel). Those towels were dried in a constant temperature and humidity room at 25° C. and 40% RH for 24 hours. Evaluation of softness and water absorption was performed on respective towels in accordance with the following evaluation criteria. The results are shown in Table 2.

(Softness)

The liquid softener composition of Comparative example 1 was used as a control (standard) and was compared with other bases. The softness was evaluated by the following evaluation criteria:

+1: Slightly softer than the control;

0: Same as the control; and

−1: The control is slightly softer.

(Water Absorption)

Each of the cotton towels (T. W220, white, manufactured by Takei Towel Co., Ltd.) was subjected to the above-described treatment and humidity-conditioned in a constant temperature and humidity room at 25° C./40% RH. A 2.5 cm×25 cm square test cloth was cut out from the plain-weave portion of each of the towels. The lower end of the test cloth was dipped into water at 25° C. After 15 minutes, the height where the water was spread up in the cloth was measured.

TABLE 1

| | | Quaternary ammonium salt | | |
|---|---|---|---|---|
| | | Symbol | Formula | Structure |
| Production example | 1 | Compound 1 | (I) | R1CO, R2CO: stearic acid residue, R3, R4: methyl group, k, l: 6, X—: Cl— |
| | 2 | Compound 2 | (II) | R5CO, R6CO: stearic acid residue, R7, R8: methyl group, m, n: 1, X'—: Cl— |
| | 3 | Compound 3 | (II) | R5CO, R6CO: stearic acid residue, R7, R8: methyl group, m, n: 2, X'—: Cl— |
| | 4 | Compound 4 | (II) | R5CO, R6CO: stearic acid reidue, R7, R8: methyl group, m, n: 3, X'—: Cl— |
| | 5 | Compound 5 | (I) | R1CO, R2CO: stearic acid residue, R3, R4: methyl group, k, l: 5, X—: Cl— |

TABLE 2

| | | Liquid softener composition | | | Evaluation | | |
|---|---|---|---|---|---|---|---|
| | | Quaternary ammonium salt | | Potassium chloride | | water-absorption | Dispersibility, |
| | | kind | weight % | weight % | softness | (cm) | handling property |
| Example | 1 | Compound 1 | 5 | 0.01 | 0 | 13.0 | Easiness in uniform dispersion Good handling property |
| | 2 | Compound 1:compound 3 = 6:4 (weight ratio) | 5 | 0.01 | +1 | 12.0 | Easiness in uniform dispersion Good handling property |
| | 3 | Compound 5 | 5 | 0.01 | +1 | 12.5 | Easiness in uniform dispersion Good handling property |
| Comparative example | 1 | Compound 2 | 5 | 0.01 | Standard | 9.8 | Difficulty in dispersion |
| | 2 | Compound 3 | 5 | 0.01 | +1 | 8.7 | Easiness in dispersion Low handling properties |
| | 3 | Compound 4 | 5 | 0.01 | +1 | 11.1 | Easiness in dispersion Low handling properties |

The invention claimed is:

1. A softener composition, comprising a quaternary ammonium salt represented by formula (I):

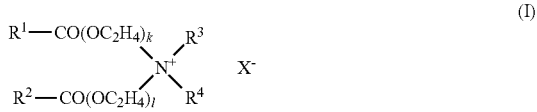
(I)

wherein $R^1$ and $R^2$ may be the same as or different from each other and represent a hydrocarbon group having 11 to 23 carbon atoms, $R^3$ and $R^4$ may be the same as or different from each other and represent a hydrocarbon group having 1 to 4 carbon atoms which may have a hydroxyl group, k and l may be the same as or different from each other and represent an integer of 5 to 10 and $X^-$ represents an anion.

2. A softener composition, comprising a quaternary ammonium salt represented by the formula (I):

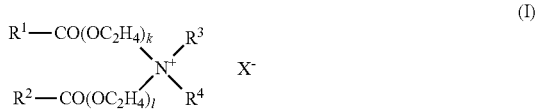
(I)

wherein $R^1$ and $R^2$ may be the same as or different from each other and represent a hydrocarbon group having 11 to 23 carbon atoms, $R^3$ and $R^4$ may be the same as or different from each other and represent a hydrocarbon group having 1 to 4 carbon atoms which may have a hydroxyl group, k and l may be the same as or different from each other and represent an integer of 5 to 10 and $X^-$ represents an anion, and a quaternary ammonium salt represented by formula (II):

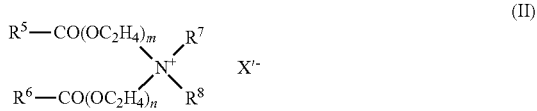
(II)

wherein $R^5$ and $R^6$ may be the same as or different from each other and represent a hydrocarbon group having 11 to 23 carbon atoms, $R^7$ and $R^8$ may be the same as or different from each other and represent a hydrocarbon group having 1 to 4 carbon atoms which may have a hydroxyl group, m and n may be the same as or different from each other and represent an integer of 2 or 3 and $X^-$ represents an anion.

3. The softener composition according to claim 2, wherein the weight ratio of the quaternary ammonium salt (I) to the quaternary ammonium salt (II) is the quaternary ammonium salt (I):the quaternary ammonium salt (II) of 99:1 to 50:50.

4. A method for producing the softener composition according to claim 1, comprising the following steps 1 and 2 as a step of producing the quaternary ammonium salt represented by the formula (I):

step 1: producing a bis(polyalkoxyalkanol)alkylamine or a bis(polyalkoxyalkanol)hydroxyalkylamine by a reaction of a halopoly alkoxy alkanol with an amine represented by the following formula (III):

$R^3$—$NH_2$ (III)

wherein $R^3$ represents a hydrocarbon group having 1 to 4 carbon atoms which may have a hydroxyl group; and step 2: esterifying the bis(polyalkoxyalkanol)alkylamine or the bis(polyalkoxyalkanol)hydroxyalkylamine produced in the step 1 with fatty acids or a derivative thereof and quaternizing the ester.

5. A method for producing the softener composition according to claim 2, comprising the following steps 1 and 2 as a step of producing the quaternary ammonium salt represented by the formula (I):

step 1: producing a bis(polyalkoxyalkanol)alkylamine or a bis(polyalkoxyalkanol)hydroxyalkylamine by a reaction of a halopoly alkoxy alkanol with an amine represented by the following formula (III):

$R^3$—$NH_2$ (III)

wherein $R^3$ represents a hydrocarbon group having 1 to 4 carbon atoms which may have a hydroxyl group; and step 2: esterifying the bis(polyalkoxyalkanol)alkylamine or the bis(polyalkoxyalkanol)hydroxyalkylamine produced in the step 1 with fatty acids or a derivative thereof and quaternizing the ester.

* * * * *